(12) United States Patent
Hirabayashi et al.

(10) Patent No.: US 8,394,401 B2
(45) Date of Patent: Mar. 12, 2013

(54) ANTIOBESITY OR ANTIHYPERLIPIDEMIC FOOD, FEEDING STUFF OR SUPPLEMENT CONTAINING LYSINE

(75) Inventors: Yuri Hirabayashi, Kawasaki (JP);
Hitoshi Murakami, Kawasaki (JP);
Hisamine Kobayashi, Kawasaki (JP);
Takeo Ueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1418 days.

(21) Appl. No.: 11/115,136

(22) Filed: Apr. 27, 2005

(65) Prior Publication Data

US 2005/0249781 A1 Nov. 10, 2005

(30) Foreign Application Priority Data

Apr. 28, 2004 (JP) ................ 2004-134683

(51) Int. Cl.
*A61K 47/00* (2006.01)
*A61K 31/198* (2006.01)
(52) U.S. Cl. ......... 424/439; 514/566; 424/400; 424/441
(58) Field of Classification Search .......... 424/439, 424/400, 441; 514/566
See application file for complete search history.

(56) References Cited

U.S. PATENT DOCUMENTS

| | | | |
|---|---|---|---|
| 4,937,234 A * | 6/1990 | Fahim | 514/53 |
| 6,004,926 A * | 12/1999 | Shimizu et al. | 514/2 |
| 6,013,622 A | 1/2000 | Bruno et al. | |
| 6,475,530 B1 * | 11/2002 | Kuhrts | 424/725 |
| 6,541,026 B2 * | 4/2003 | Siskind | 424/439 |
| 2004/0171690 A1 | 9/2004 | Ammann et al. | |
| 2004/0234631 A1 * | 11/2004 | Hoie | 424/757 |

FOREIGN PATENT DOCUMENTS

| | | |
|---|---|---|
| JP | 61-215323 | 9/1986 |
| JP | 1-98445 | 4/1989 |
| JP | 6-24977 | 2/1994 |
| JP | 8-140626 | 6/1996 |
| JP | 9-157163 | 6/1997 |
| JP | 2002-511392 | 4/2002 |
| JP | 2003-119133 | 4/2003 |
| JP | 2004-321171 | 11/2004 |
| WO | 02/087562 | 11/2002 |

OTHER PUBLICATIONS

U.S. Appl. No. 11/847,939, filed Aug. 30, 2007, Hirabayashi, et al.
I. Giroux et al, "Role of dietary lysine, methionine, and arginine in the regulation of hypercholesterolemia in rabbits", *Journal of Nutritional Biochemistry* Mar. 1999, vol. 10, pp. 166-171.
T. Yamamoto et al, "Amino Acids Diet", published by Goma-shobo Publishing Co., 2002, p. 17.
T. Sanjo, "Amino Acids Diet", published by Nitto-shoin Publishing Co., 2002, p. 24.
T. Sanjo, "Rapidly Get into Better Health with Amino Acids!!", published by Mikasa-shobo Publishing Co., 2001, p. 79.

\* cited by examiner

*Primary Examiner* — Jason M Sims
*Assistant Examiner* — Zohreh Vakili
(74) *Attorney, Agent, or Firm* — Oblon, Spivak, McClelland, Maier & Neustadt, L.L.P.

(57) ABSTRACT

In this application, an antiobesity or antihyperlipidemic food, feeding stuff or supplement containing lysine component(s) that is characterized in that said food, feeding stuff or supplement contains lysine component(s) at such rate that 40 to 160 mg in terms of free-form lysine should be taken in per kg of body weight per day, under diet conditions under which the daily protein energy composition is 20% or less, and an antiobesity or antihyperlipidemic food, feeding stuff or supplement containing lysine component(s) that is characterized by containing said lysine component(s) in an amount of 0.8 to 3.0 wt % in terms of free-form lysine on the basis of the dry matter and having a protein energy composition of 20% or less are disclosed. According to the present invention, a method that can realize a reduction in body weight or body fat, suppress weight increases, or improve hyperlipidemia for obese persons or persons concerned about increases in their body weight, safely and to the fullest extent and a method that can eliminate the fat of unnecessarily obese animals, or control obesity, can be provided.

6 Claims, 4 Drawing Sheets

Fig. 1: Body Weight after 8 Weeks of the Experimental Period
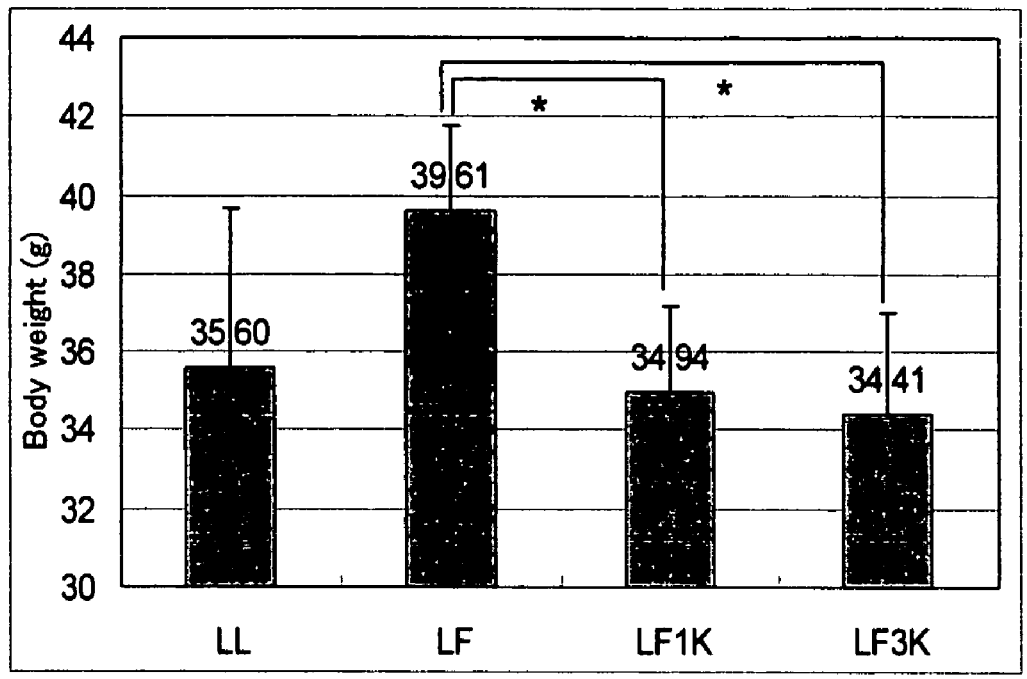
Fig. 2: Total Fat Weight
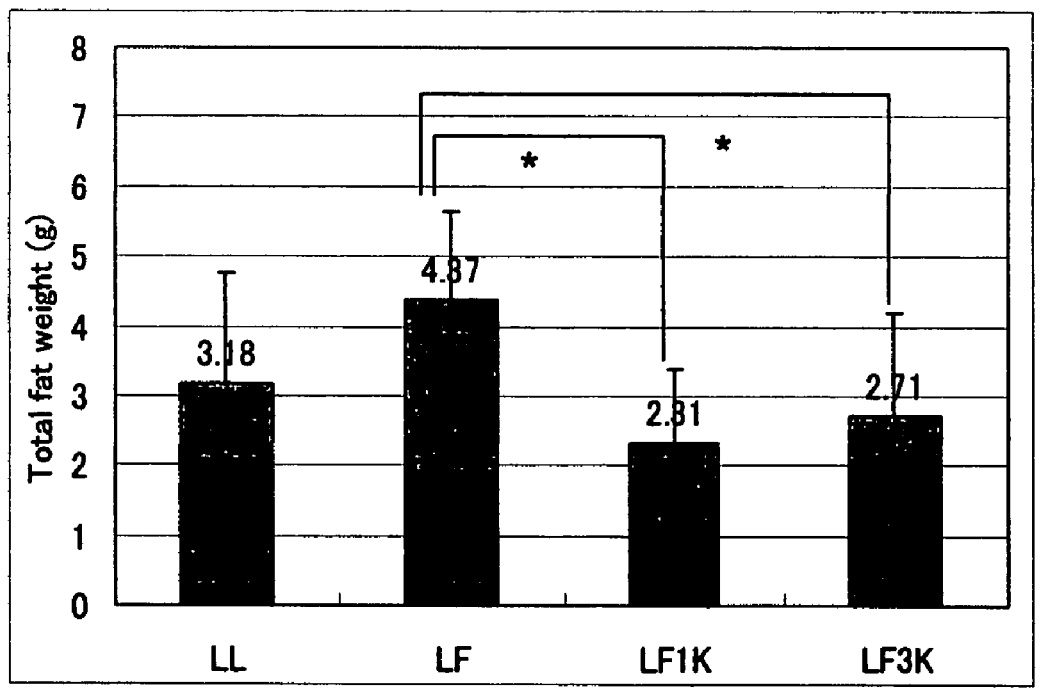

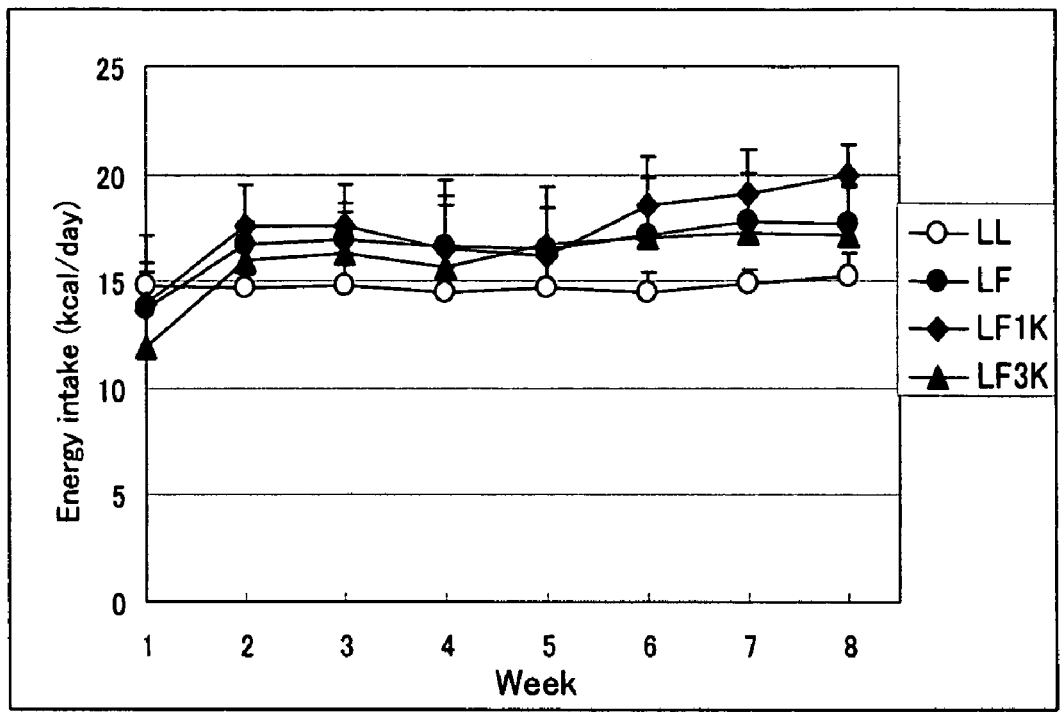
Fig. 3: Changes of Energy Intake
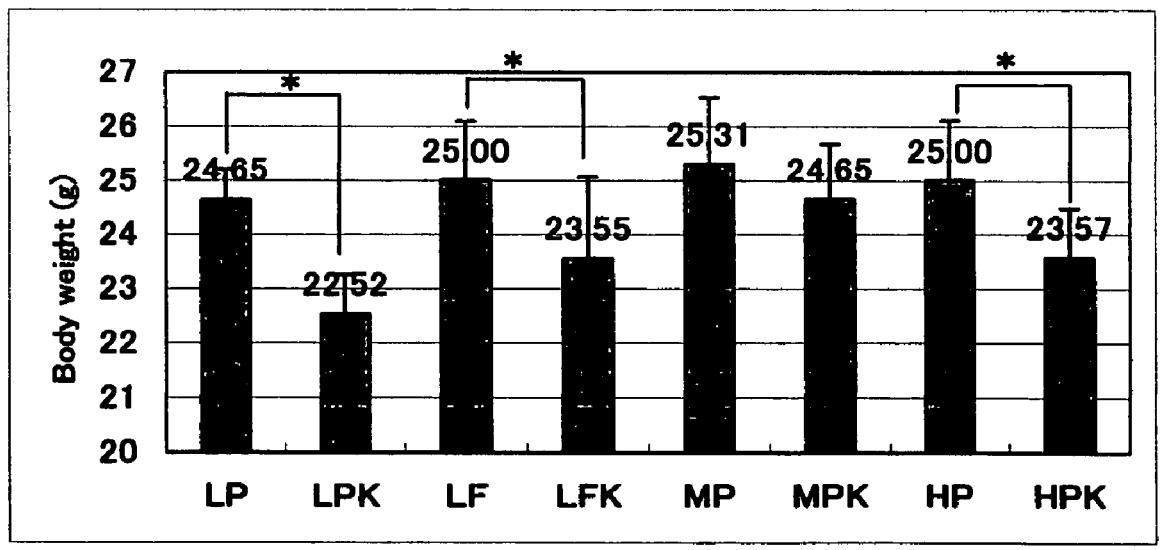
Fig. 4: Body Weight after 4 Weeks

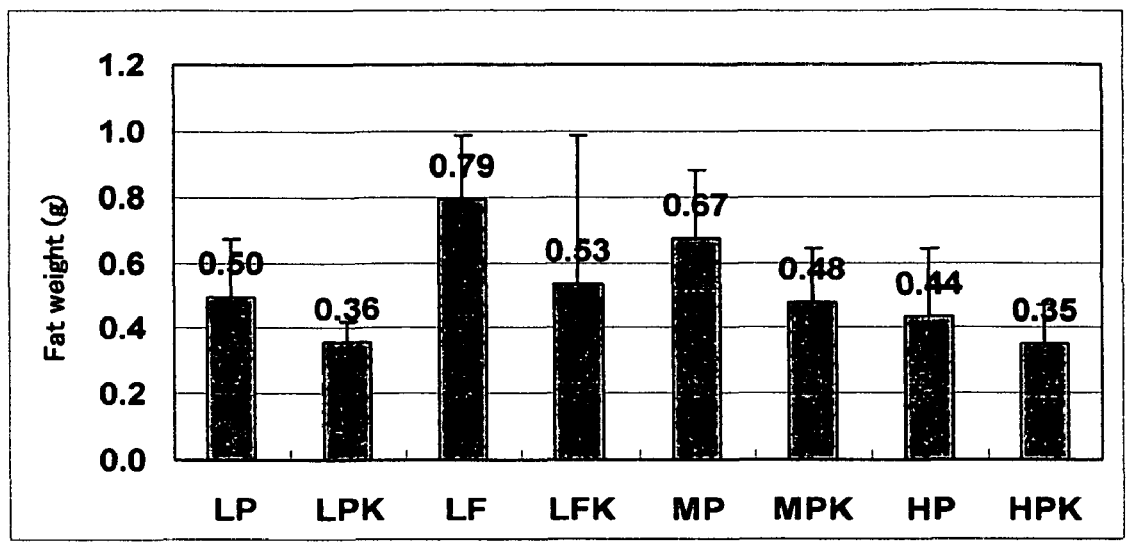
Fig. 5: Total Fat Weight after 4 Weeks
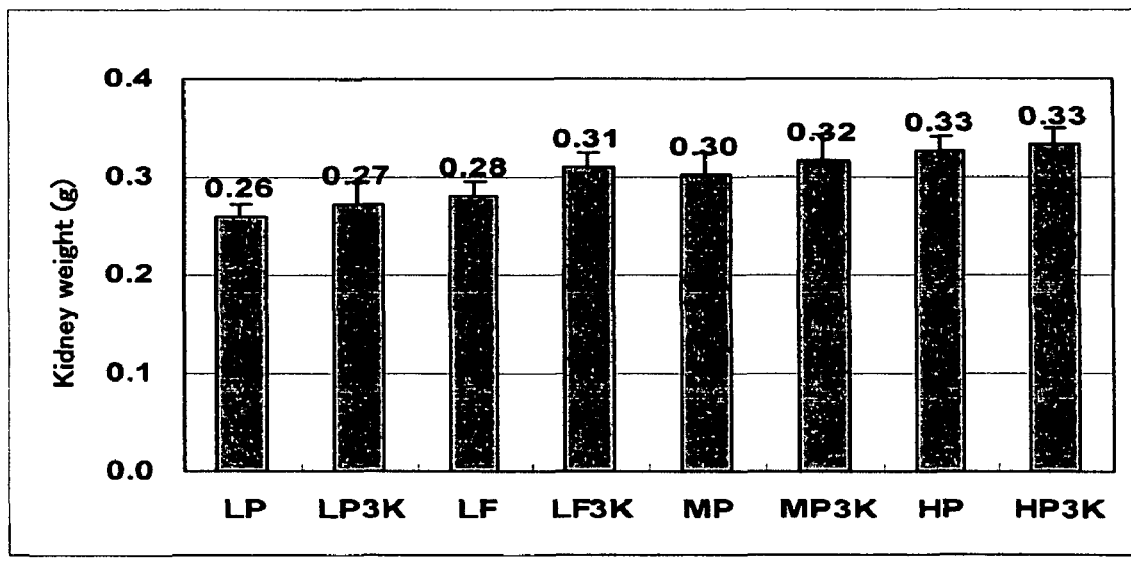
Fig. 6: Kidney Weight after 4 Weeks

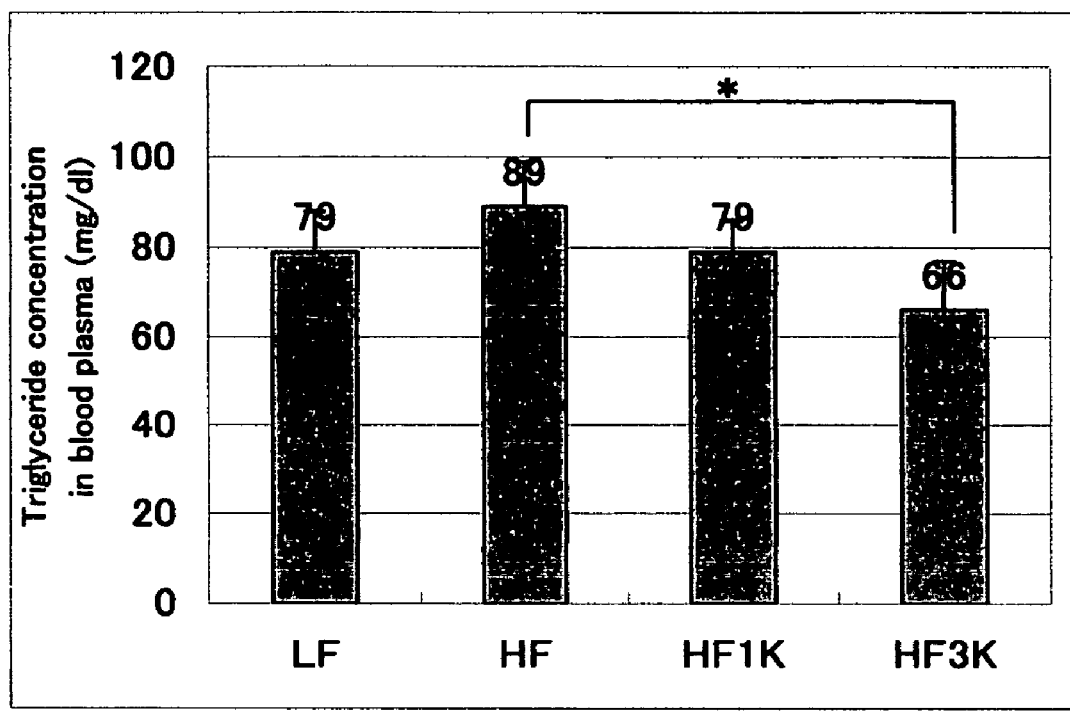
Fig. 7: Triglyceride Concentration in Blood Plasma

ANTIOBESITY OR ANTIHYPERLIPIDEMIC FOOD, FEEDING STUFF OR SUPPLEMENT CONTAINING LYSINE

CROSS REFERENCES TO RELATED APPLICATIONS

This application claims priority to Japanese Patent Application No. 2004-134683, filed on Apr. 28, 2004.

TECHNICAL FIELD OF THE INVENTION

The present invention relates to a food for ingestion by an obese person or a person concerned about an increase in body weight in order to reduce his or her body weight or body fat. The present invention also relates to a feeding stuff that is useful for eliminating fat of animals such as livestock and zoo animals or pets reared indoors or in a narrow enclosure and fed with concentrated feed and which have become fat due to a lack of exercise or the like.

BACKGROUND ART

An increase in the number of obese people has become a serious social problem in recent years. Obesity is a major cause of adult diseases such as diabetes and arteriosclerosis, and there is thus an earnest desire to reduce obesity.

In recent years attention has been focused oh the physiological actions of amino acids, and expectations have grown with respect to the antiobestic effect of amino acids. Among these, it has been reported that lysine, arginine, proline and phenylalanine have an antiobesity action and are referred to as diet amino acids, and, however, the grounds and effects thereof have not been sufficiently clarified. See T. Yamamoto (general supervising editor), "Amino Acids Diet", published by Goma-shobo publishing Co., in 2002, and T. Sanjo (general supervising editor), "Amino Acids Diet", published by Nitto-shoin publishing Co., in 2002.

Further, it has been reported that as a meal composition that exerts the maximum diet effect of amino acids, a ratio of protein:fat:carbohydrate is preferably 6:1:3. See T. Sanjo (general supervising editor), "Rapidly Get into Better Health with Amino Acids!!", published by Mikasa-shobo publishing Co., in 2001. However, ingestion of this kind of high-protein diet is difficult from the practical viewpoint and, in addition, when a diet contains an extremely large amount of protein, the burden on the liver and the kidney is increased, and it cannot be considered desirable from the safety viewpoint. Therefore, there is a pressing need to clarify conditions that can ensure the safety of a composition as a food and also exert the effect to the fullest extent.

Meanwhile, the aforementioned problem of obesity has also been occurring in animals such as pets or zoo animals and other animals in recent years.

DISCLOSURE OF THE INVENTION

Problems to be Solved by the Invention

In view of the circumstances of the background art as described in the foregoing, it is an object of the present invention to provide a method that can realize a reduction in body weight or body fat, suppress weight increases, or improve hyperlipidemia for obese persons or persons concerned about increases in their body weight, safely and to the fullest extent. It is another object of the present invention to provide a method that can eliminate the fat of unnecessarily obese animals, or control obesity.

Means for Solving the Problems

The present inventors have carried out concentrated studies to achieve the aforementioned objects and, as results, found that, when the daily intake of free-form lysine, lysine salts or/and lysine in peptide form (one or more of these being referred to hereinafter collectively as "lysine component(s)") is from 40 to 160 mg per kg of body weight, or the lysine component content in a food or a feeding stuff is from 0.8 to 3.0 wt % on the dry matter basis and at the same time, the protein energy composition is 20% or less, it is possible to suppress increases in body weight and body fat and also improve hyperlipidemia, safely and to the fullest extent. On these findings has been completed the present invention.

Accordingly, the present invention relates to an antiobesity or antihyperlipidemic food, feeding stuff or supplement containing lysine component(s) that is characterized in that said food, feeding stuff or supplement contains lysine component(s) at such rate that 40 to 160 mg in terms of free-form lysine should be taken in per kg of body weight per day, under ingestive or feeding conditions under which the daily protein energy composition is 20% or less, and to an antiobesity or antihyperlipidemic food, feeding stuff or supplement containing lysine component(s) that is characterized by containing said lysine component(s) in an amount of 0.8 to 3.0 wt % in terms of free-form lysine on the basis of the dry matter and having a protein energy composition of 20% or less.

Effect of the Invention

The present invention relates to an antiobesity or antihyperlipidemic food, a feeding stuff or a supplement for which a daily intake of free-form lysine, lysine salts or/and lysine in peptide form should be from 40 to 160 mg per kg of body weight, or to an antiobesity or antihyperlipidemic food, a feeding stuff or a supplement the lysine component content of which is from 0.8 to 3.0 wt % in terms of free-form lysine on the basis of dry matter and protein energy composition which is 20% or less. By ingestion of the inventive food, feeding stuff or supplement, an increase in body weight and body fat can be suppressed and hyperlipidemia can be improved, safely and to the fullest extent without ingesting high protein food as described in the aforementioned book entitled "Rapidly Get into Better Health with Amino Acids!!", that is, under the conditions under which the protein energy composition is 20% or less, preferably less than 15%, and more preferably 10%. This can also be achieved with respect to the fatness of animals.

BRIEF DESCRIPTION OF THE DRAWINGS

FIG. 1 shows the body weight after 8 weeks of the experimental period (Experimental Example 1).

FIG. 2 shows the total fat weight after 8 weeks of the experimental period (Experimental Example 1).

FIG. 3 shows the changes of energy intake during the experimental period (Experimental Example 1).

FIG. 4 shows the body weight after 4 weeks of the experimental period (Experimental Example 2).

FIG. 5 shows the total fat weight after 4 weeks of the experimental period (Experimental Example 2).

FIG. 6 shows the kidney weight after 4 weeks of the experimental period (Experimental Example 2).

FIG. 7 shows the triglyceride concentration in blood plasma after 4 weeks of the experimental period (Experimental Example 3).

DETAILED DESCRIPTION OF THE INVENTION

Target subjects for ingestion or feeding of the antiobesity or antihyperlipidemic food, feeding stuff or supplement containing lysine component(s) of the present invention are humans and animals, and such animals include pets such as dogs, cats, rabbits, ferrets, hamsters, birds, and the like and zoo animals, as well as livestock (industrial animals) such as (race) horses, cows, sheep, pigs, birds, and the like, and the animals are not particularly limited as long as there is a concern that the animal may become unnecessarily fat.

The lysine to be used according to the present invention may be of any form as long as the lysine is in the free form, the salt form or the peptide form. The lysine may be in the L-form, D-form or DL-form. Naturally, the various forms of lysine may be used in combinations of two or more kinds. For example, there may be mentioned as lysine salts, lysine hydrochloride, lysine acetate, lysine glutamate and lysine aspartate, and as lysine in peptide form there may be mentioned oligopeptides and the like, containing lysine such as lysyl-lysine and the like. Of these, at the time of ingestion by humans, the use of L-lysine hydrochloride, L-lysine acetate and L-lysine glutamate in the salt forms are particularly preferable from the viewpoint of ingestion experience.

As a lysine intake amount to be ingested per day, 40 to 160 mg per kg of human weight is preferable, and more preferably, it is 60 to 120 mg. In the case of animals, a lysine content included in a feeding stuff is preferably 0.8 to 3.0 wt % (dry matter basis), and more preferably, it is 1.2 to 2.25 wt %. When the amount or content is less than 40 mg or 0.8 wt %, the effect may be weakened and a clearer effect cannot be expected. Further, although the maximum acceptable intake of amino acids is not established, when the amount or content exceeds 160 mg or 3.0 wt %, it may merely result in the ingestion of a large amount of a sigle amino acid which is, in turn, not preferable from the viewpoint of amino acid balance. In this connection, although there are a variety of forms of lysine, the term "lysine intake weight" as used herein in connection of the present invention refers to the weight amount of lysine in terms of the free form thereof. In addition, when a protein energy composition is 20% or less, more preferably less than 15%, an increase in body weight and body fat can be suppressed safely and to the fullest extent.

Further, when the usage conditions are the same as those described in the preceding paragraph, there can be obtained an improvement effect for hyperlipidemia that accompanies lipid metabolism abnormality due to obesity, diabetes or the like.

For the food or feeding stuff of the present invention prepared in combination with lysine component(s), it is necessary that a protein energy composition be 20% or less. The term "protein energy composition" as used herein refers to the proportion of the proteins when energy conversion is conducted, i.e., in terms of energy in kcal derivable therefrom, for the nutrients (protein, fat, and carbohydrate) included in the food or feeding stuff (protein: 4.240 kcal/g, fat: 9.461 kcal, and carbohydrate: 4.183 kcal/g). The same applies for the fat energy composition. As long as the protein energy composition is 20% or less, the food or feeding stuff may be compounded with other nutrients such as carbohydrates, lipids, proteins, vitamins, minerals, and the like. At that time, these nutrients can be combined with, for example, an excipient such as dextrin, or the like, a taste-improving substance such as vanillin or the like, a coloring agent such as a safflower color agent and the like. Although the energy composition of the other nutrients is not particularly limited according to the present invention, the fat energy composition is preferably 20 to 25%.

According to the present invention, lysine component(s) may be provided for use in the form of a so-called supplement is separated from the inventive food or a feeding stuff, and also be provided for use in the form of a food or a feeding stuff which is added with lysine component(s). Regarding the form of such a product, a product can be put on the market for distribution in the form of a powder or liquid mixture or the like. Further, regarding the product classification, a product can be provided for distribution as a supplement (including weight-loss clinics for pets), a beverage, a condiment, a processed food and the like.

Regarding the specific manners of ingestion or feeding, there are no limitations concerning the frequency or timing of the intake as long as the inventive composition (food, feeding stuff or supplement) is taken in, i.e., ingested or fed, in the form such as a physiologically functional food, a feeding stuff for animals, or the like, containing lysine component(s) in an amount of 0.8 to 3.0 wt % in terms of the free-form lysine, a supplement containing lysine component(s) in an amount of 40 to 160 mg in terms of free form lysine is ingested per kg of human body weight per day, or in the case of animal feeds, 4 to 15% of a protein intake is fed in the form of the inventive feeding stuff. Preferably, the lysine component(s) are taken in together with a meal, or in the same amounts before and after a meal, respectively.

Finally, the intake amount of lysine component(s) and a food or a feeding stuff and of a food or a feeding stuff containing lysine component(s) of the present invention will be described hereunder.

When a feeding stuff having a 20% protein energy was given to mice and the supplemented amount of lysine component(s) per feeding was 0.8 to 3.0 wt % on the dry matter basis, it was observed that an increase in body weight and body fat was suppressed safely and to the fullest extent, and that an improvement effect for hyperlipidemia was exhibited. Since the daily protein intake by humans (for example, Japanese people) is about 1 g per kg of body weight, and when this is converted to the daily intake for lysine component(s), that yields an amount of 40 to 160 mg per kg of body weight.

EXAMPLES

Experimental Example 1

A high fat diet (dietary energy composition ratio was protein:fat:carbohydrate=17:46:37) was provided for 16 weeks to 30 5-week-old C57BL/6J male mice. At the 16th week, the 30 mice were divided into 3 groups, each consisting of 10 individuals (n=10), and from then, the following diets were provided for 8 weeks to the 3 groups, respectively, (1) 20% protein energy diet (LF; protein:fat:carbohydrate=2:7:1), (2) 20% protein energy diet supplemented with 1% lysine hydrochloride (LF1K; containing 1% lysine hydrochloride (0.8% lysine base)), and (3) 20% protein energy diet supplemented with 3% lysine hydrochloride (LF3K; containing 3% lysine hydrochloride (2.4% lysine base)). Herein, the term "lysine base" refers to free-form lysine. Further, as a nonobese group, a group (LL) was prepared consisting of 10 mice of the same species that were fed with 20% protein energy diet (protein:fat:carbohydrate=2:7:1) from the start of the experiment until the end, i.e., for 24 weeks. The compositions of the diets are shown in Table 1.

TABLE 1

Compositions of the Diets

| | | LF | LF1K | (wt. %) LF3K |
|---|---|---|---|---|
| Protein | Casein | 20.00 | 20.00 | 20.00 |
| | L-Cystine | 0.30 | 0.30 | 0.30 |
| | L-Lysine hydrochloride | 0.00 | 1.00 | 3.00 |
| Carbohydrate | β-Cornstarch | 51.75 | 50.75 | 48.75 |
| | α-Cornstarch | 13.20 | 13.20 | 13.20 |
| Fat | Soybean oil | 5.00 | 5.00 | 5.00 |
| | Cellulose | 5.00 | 5.00 | 5.00 |
| | Minerals mixture (AIN-93G) | 3.50 | 3.50 | 3.50 |
| | Vitamins mixture (AIN-93) | 1.00 | 1.00 | 1.00 |

TABLE 1-continued

Compositions of the Diets

|  | LF | LF1K | LF3K (wt. %) |
|---|---|---|---|
| Choline hydrogen tartrate | 0.25 | 0.25 | 0.25 |
| t-Butylhydroquinone | 0.0014 | 0.0014 | 0.0014 |
| Total | 100.00 | 100.00 | 100.00 |

The food intakes were measured and the energy intakes were determined from the energy per g of each test diet. After 8 weeks of the experimental period, the body weight and the total fat weight (sum of epididymal fat, perirenal fat, mesenteric fat, and subcutaneous fat in the periphery of the femoral region) were measured. The results will be shown in FIGS. 1 to 3 attached hereto. Statistical analysis was performed using Dunnett's test employing the LF group as the control. The * symbol in the figures indicates that $p<0.05$.

FIG. 1 shows the body weight upon the autopsy and FIG. 2 shows the total fat weight. A significant decrease in body weight and total fat weight that was dose-dependent of the lysine component(s) was observed, showing that the inventive compositions are useful as a substance that possesses an antiobesity action. FIG. 3 shows changes of energy intake. A significant difference was not observed between the groups, indicating that the effect to suppress the accumulation of body fat by lysine supplementation was not caused by anorexia.

Experimental Example 2

The following feeding stuffs were respectively provided for 4 weeks to 8 groups of 9-week-old C57BL/6J male mice, consisting of 10 individuals per group (n=10): (1) 10% protein energy diet (LP; dietary energy composition ratio was protein:fat:carbohydrate=1:1:8), (2) 10% protein energy diet supplemented with lysine hydrochloride (LPK), (3) 20% protein energy diet (LF; protein:fat:carbohydrate=2:1:7), (4) 20% protein energy diet supplemented with lysine hydrochloride (LFK), (5) 40% protein energy diet (MP; protein:fat:carbohydrate=4:1:5), (6) 40% protein energy diet supplemented with lysine hydrochloride (MPK), (7) 60% protein energy diet (HP; protein:fat:carbohydrate=6:1:3), and (8) 60% protein energy diet supplemented with lysine hydrochloride (HPK). The diets, when supplemented with lysine hydrochloride, were added with 3% lysine hydrochloride. The compositions of the diets are shown in Table 2.

After 4 weeks the experimental period, the body weight, the total fat weight(sum of epididymal fat, perirenal fat, mesenteric fat, and subcutaneous fat in the periphery of the femoral region), and the kidney weight were measured. The results will be shown in FIGS. 4 to 6 attached hereto. Statistical analysis was performed using Dunnett's test, employing the respective groups fed with the diets without lysine supplementation as the controls. The * symbol in the figures indicates that $p<0.05$.

FIG. 4 shows the body weight after 4 weeks of the experimental period and FIG. 5 shows the total fat weight. A decrease in body weight and total fat weight caused by supplementing each diet with the lysine hydrochloride was observed, and in particular, a significant decrease in body weight was observed for the LPK group, MPK group and HPK group. FIG. 6 shows the kidney weight. The kidney weight became heavier in line with an increase in the protein amount in the diets, and a load on the kidney due to ingestion of high protein diet was confirmed. Hence, it was shown that the antiobesity action of the lysine (component's) according to the present invention exhibits a safe and maximum effect when the protein energy composition is 20% or less.

Experimental Example 3

The following diets were respectively provided for 8 weeks to 4 groups of 9-week-old C57BL/6J male mice, consisting of 10 individuals per group (n=10): (1) 20% protein energy diet (LF; dietary energy composition ratio was protein:fat:carbohydrate=2:7:1), (2) high fat feed (HF; protein:fat:carbohydrate=17:46:37), (3) high fat food supplemented with 1% lysine hydrochloride (HF1K; containing 1% lysine hydrochloride (0.8% lysine base)), and (4) high fat feed supplemented with 3% lysine hydrochloride (HF3K; containing 3% lysine hydrochloride (2.4% lysine base)). The compositions of the diets are shown in Table 3.

TABLE 2

Compositions of the Diets

|  |  | LP | LPK | LF | LFK | MP | MPK | HP | HPK (wt. %) |
|---|---|---|---|---|---|---|---|---|---|
| Protein | Casein | 9.50 | 9.22 | 20.00 | 19.40 | 38.00 | 36.86 | 57.00 | 55.29 |
|  | L-Cystine | 0.30 | 0.29 | 0.30 | 0.29 | 0.30 | 0.29 | 0.30 | 0.29 |
|  | L-Lysine hydrochloride | 0.00 | 3.00 | 0.00 | 3.00 | 0.00 | 3.00 | 0.00 | 3.00 |
| Carbohydrate | β-Cornstarch | 62.75 | 60.87 | 52.25 | 50.68 | 34.25 | 33.22 | 15.25 | 14.79 |
|  | α-Cornstarch | 13.20 | 12.80 | 13.20 | 12.80 | 13.20 | 12.80 | 13.20 | 12.80 |
| Fat | Soybean oil | 4.50 | 4.37 | 4.50 | 4.37 | 4.50 | 4.37 | 4.50 | 4.37 |
|  | Cellulose | 5.00 | 4.85 | 5.00 | 4.85 | 5.00 | 4.85 | 5.00 | 4.85 |
|  | Minerals mixture (AIN-93G) | 3.50 | 3.40 | 3.50 | 3.40 | 3.50 | 3.40 | 3.50 | 3.40 |
|  | Vitamins mixture (AIN-93) | 1.00 | 0.97 | 1.00 | 0.97 | 1.00 | 0.97 | 1.00 | 0.97 |
|  | Choline hydrogen tartrate | 0.25 | 0.24 | 0.25 | 0.24 | 0.25 | 0.24 | 0.25 | 0.24 |
|  | t-Butylhydroquinone | 0.0014 | 0.0014 | 0.0014 | 0.0014 | 0.0014 | 0.0014 | 0.0014 | 0.0014 |
|  | Total | 100.00 | 100.00 | 100.00 | 100.00 | 100.00 | 100.00 | 100.00 | 100.00 |

TABLE 3

| | | LF | HF | HF1K | (wt. %) HF3K |
|---|---|---|---|---|---|
| Protein | Casein | 20.00 | 20.00 | 20.00 | 20.00 |
| | L-Cystine | 0.30 | 0.30 | 0.30 | 0.30 |
| | L-Lysine hydrochloride | 0.00 | 0.00 | 1.00 | 3.00 |
| Carbohydrate | β-Cornstarch | 51.75 | 31.75 | 30.75 | 28.75 |
| | α-Cornstarch | 13.20 | 13.20 | 13.20 | 13.20 |
| Fat | Coconut oil | 0.00 | 4.00 | 4.00 | 4.00 |
| | Soybean oil | 5.00 | 21.00 | 21.00 | 21.00 |
| | Cellulose | 5.00 | 5.00 | 5.00 | 5.00 |
| | Minerals mixture (AIN-93G) | 3.50 | 3.50 | 3.50 | 3.50 |
| | Vitamins mixture (AIN-93) | 1.00 | 1.00 | 1.00 | 1.00 |
| | Choline hydrogen tartrate | 0.25 | 0.25 | 0.25 | 0.25 |
| | t-Butylhydroquinone | 0.0014 | 0.0014 | 0.0014 | 0.0014 |
| | Total | 100.00 | 100.00 | 100.00 | 100.00 |

After 8 weeks of the experimental period, the triglyceride concentration in the blood plasma was measured. The results will be shown in FIG. 7 attached hereto. Statistical analysis was performed using Dunnett's test employing the HF group as the control. The * symbol in the figure indicates that $p<0.05$.

The results shown in FIG. 7 reveals that an increase in the triglyceride concentration in the blood plasma due to intake of the high fat diet was significantly inhibited by the lysine supplementation, and that the lysine has an antihyperlipidemic effect.

The invention claimed is:

1. An antiobesity or antihyperlipidemic food or supplement, which comprises at least one lysine component selected from the group consisting of lysine, a lysine salt, an oligopeptide which contains at least one lysine residue, and mixtures thereof, wherein:
   the food or supplement comprises the at least one lysine component in an amount of 0.8 to 3.0 wt % in terms of free-form lysine on the basis of dry matter in the food or supplement; and
   the food or supplement has a protein energy component of less than 15%.

2. The food or supplement of claim 1, wherein the at least one lysine component is selected from the group consisting of L-lysine hydrochloride, L-lysine acetate, L-lysine glutamate, and mixtures thereof.

3. An antiobesity or antihyperlipidemic animal feed or animal feed supplement, which comprises at least one lysine component selected from the group consisting of lysine, a lysine salt, an oligopeptide which contains at least one lysine residue, and mixtures thereof, wherein:
   the food or supplement comprises the at least one lysine component in an amount of 0.8 to 3.0 wt % in terms of free-form lysine on the basis of dry matter in the food or supplement; and
   the animal feed or animal feed supplement has a protein energy component of less than 15%.

4. The animal feed or animal feed supplement of claim 3, wherein the at least one lysine component is selected from the group consisting of L-lysine hydrochloride, L-lysine acetate, L-lysine glutamate, and mixtures thereof.

5. The food or supplement of claim 1, wherein the at least one lysine component is L-lysine hydrochloride.

6. The food or supplement of claim 3, wherein the at least one lysine component is L-lysine hydrochloride.

* * * * *